(12) United States Patent
Braun et al.

(10) Patent No.: US 7,057,079 B2
(45) Date of Patent: Jun. 6, 2006

(54) METHOD OF SYNTHESIZING ALKENONE COMPOUNDS

(75) Inventors: Max Braun, Wedemark (DE); Uta Claassen, Hohenhameln (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 10/912,587

(22) Filed: Aug. 6, 2004

(65) Prior Publication Data

US 2005/0070716 A1  Mar. 31, 2005

Related U.S. Application Data

(63) Continuation of application No. PCT/EP03/00913, filed on Jan. 30, 2003.

(30) Foreign Application Priority Data

Feb. 8, 2002  (DE)  ............................... 102 05 224
Dec. 31, 2002  (DE)  ............................... 102 61 471

(51) Int. Cl.
  *C07C 45/45*  (2006.01)
(52) U.S. Cl. .................. 568/405; 568/319; 568/322; 568/397; 568/415
(58) Field of Classification Search ................ 568/319, 568/322, 397, 405, 415
See application file for complete search history.

(56) References Cited

U.S. PATENT DOCUMENTS 4,705,801 A  11/1987  Martin et al.
5,708,175 A *  1/1998  Koyanagi et al. ........... 546/250

FOREIGN PATENT DOCUMENTS

| DE | 10104663 | 8/2002 |
| EP | 0257605 | 3/1988 |
| EP | 623582 | 11/1994 |
| EP | 744400 | 11/1996 |
| EP | 893426 | 1/1999 |
| GB | 2305174 | 4/1997 |

OTHER PUBLICATIONS

An article by Buback et al., "Diastereoselectivity and Kinetics of Intermolecular Hetero Diels-Alder Reactions Under High Pressure. A Significant Pressure-Induced Increase in Stereo selectivity Inter- and Intromolecular Hetero Diels-Alder Reactions, Part XXVI," Chemische Berichte, vol. 122, 1989, pp. 1179-1186.

An article by Bonner et al., "Acyl Trifluoroacetates. Part IV, Trifluoroacetylation of Hydroxy-Compounds with Trifluoroacetic Anhydride," Journal of the Chemical Society Section B, vol. 1968, pp. 114-118.

An article by Sleevi et al., "Trifluoroacetyl Chloride for Characterisation of Organic Functional Groups by Fluorine-19 Nuclear Magnetic Resonance Sprectrometry," Analytical Chemistry, vol. 51, No. 12, 1979, pp. 1931-1934.

I.I. Gerus et al., "β-Ethoxyvinyl Polyfluoroalkyl Ketones-Versatile Synthones in Fluoroorganic Chemistry", Journal of Fluorine Chemistry, 1994, pp. 195-198, vol. 69, Elsevier Science S.A.

D.V. Gorlov et al., "Acylation of 2-Methoxypropene with Anhydrides and Halides of Perfluorocarboxylic Acids in the Presence of Tertiary Amines", Russian Chemical Bulletin, Sep. 1999, 1791-1792, vol. 48, No. 9, Kluwer Academic/Plenum Publishers.

Takeshi Moriguchi et al., "Addition-Elimination Reaction in the Trifluoroacetylation of Electron-Rich Olefins", J. Org. Chem., 1995, pp. 3523-3528, vol. 60, No. 11, American Chemical Society.

Agenor Colla et al. "Trihaloacetylated Enol Ethers- General Synthetic Procedure and Heterocyclic Ring Closure Reactions with Hydroxylamine", Synthesis, Jun. 1991, pp. 483-486.

Masaru Hojo et al., "Electrophilic Substitutions of Olefinic Hydrogens II. Acylation of Vinyl Ethers and N-Vinyl Amides", Chemistry Letters, 1976, pp. 499-502, Chemical Society of Japan.

John M. Mellor, et al., "Synthesis of Trifluoromethylnaphthalenes," Tetrahedron, 56, 2000, 10067-10074, Elsevier Science Ltd.

* cited by examiner

Primary Examiner—Bernard Dentz
(74) Attorney, Agent, or Firm—Crowell & Moring LLP

(57) ABSTRACT

A method of producing a halogen alkenone ether by attaching carboxylic acid halogenides or carboxylic acid anhydrides to a vinyl ether. According to the invention the method is carried out in the presence of an onium salt of a carbonic acid which can be regenerated. The resulting product is obtained in high yields. Alternatively, pyridine which is substituted by one, two or three C1–C3 alkyl groups or other onium salts can be used.

13 Claims, No Drawings

METHOD OF SYNTHESIZING ALKENONE COMPOUNDS

CROSS REFERENCE TO RELATED APPLICATIONS

This application is a continuation of international patent application no. PCT/EP03/00913, filed Jan. 30, 2003, designating the United States of America, and published in German as WO 03/066558, the entire disclosure of which is incorporated herein by reference. Priority is claimed based in Federal Republic of Germany patent application nos. DE 102 05 224.7, filed Feb. 8, 2002, and DE 102 61 471.7, filed Dec. 31, 2002.

BACKGROUND OF THE INVENTION

The present invention relates to a method for the synthesis of halogenated alkenone ethers.

Halogenated alkenone ethers, such as 4-ethoxy-1,1,1-trifluoro-3-buten-2-one, are used as building blocks in chemical synthesis. They can be synthesized by reacting an acid chloride with a vinyl ether in the presence of a base. See, for example, U.S. Pat. No. 5,708,175 (=EP 744,400).

SUMMARY OF THE INVENTION

It is an object of the present invention to provide an improved method of synthesizing alkenone compounds.

Another object of the invention is to provide a method of synthesizing alkenone compounds which produces the desired products in high yields.

These and other objects are achieved in accordance with the present invention by providing a method of synthesizing an alkenone compound corresponding to the formula:

$$R^1—C(O)—C(H)=C(H)—OR^2 \quad (I)$$

wherein

R$^1$ represents a C1 to C4 alkyl group or a C1 to C4 alkyl group substituted by at least one halogen atom, or R$^1$ represents CF$_3$C(O)CH$_2$; and R$^2$ represents aryl, substituted aryl, a C1 to C4 alkyl group or a C1 to C4 alkyl group, which is substituted by at least one halogen atom;

said method comprising:

reacting an acid anhydride or an acid halide corresponding to formula (II)

$$R^1—C(O)X \quad (II)$$

wherein

X represents R$^1$—C(O)—O or fluorine, chlorine or bromine, and R$^1$ has the meaning given above, with a vinyl ether corresponding to formula (III)

$$CH_2=C(H)—OR^2 \quad (III)$$

wherein R$^2$ has the meaning given above, in the presence of an "onium" salt of a carboxylic acid, or optionally chlorinated pyridine, substituted with one or two C1 to C3 alkyl groups, or an "onium" salt of an inorganic acid.

According to the inventive method of synthesizing alkenones of formula (I)

$$R^1—C(O)—C(H)=C(H)—OR^2 \quad (I)$$

in which R$^1$ represents a C1 to C4 alkyl group or a C1 to C4 alkyl group substituted by at least one halogen atom, or R$^1$ represents CF$_3$C(O)CH$_2$, and R$^2$ represents aryl, substituted aryl, a C1 to C4 alkyl group or a C1 to C4 alkyl group, which is substituted by at least one halogen atom, an acid anhydride or an acid halide of formula (II)

$$R^1—C(O)X \quad (II)$$

in which X represents R$^1$—C(O)—O or fluorine, chlorine or bromine and R$^1$ has the meaning given above, is reacted with a vinyl ether of formula (III)

$$CH_2=C(H)—OR^2 \quad (III)$$

in which R$^2$ has the meaning given above, in the presence of an "onium" salt of a carboxylic acid, or in which optionally chlorinated pyridine, substituted with one or two C1 to C3 alkyl groups, is used, or in which an "onium" salt of an inorganic acid is used.

Pursuant to a variation of the invention, pyridine, substituted by one, two or three C1 to C3 alkyl groups, preferably picoline, collidine or lutidine (that is, pyridine, substituted by one, two or three methyl groups, all isomers being usable) and preferably 2-picoline, is used. The pyridine, substituted by one to three C1 to C3 alkyl groups, may also be substituted by one or more chlorine atoms in the ring and/or in the alkyl group or groups. Moreover, chloromethylpyridine, dichloromethyl-pyridine, and trichloromethylpyridine, and especially the picoline substituted in the 2 position, is preferred. Even if the hydrochloride formed were to be burned or deposited in a landfill, this variation is advantageous compared to other amines used in the state of the art, because of the higher yield, which is achieved (however, is possible to recycle by an acid treatment, as will be described further below).

In accordance with a further variation, an "onium" salt of any amine of an inorganic acid is used. It was noted that adducts of an amine and an acid, even an organic acid, act as acid interceptor in the present invention if the molar ratio of amine to acid is less than 3. For example, onium hydrochloride is able to intercept two moles of hydrogen chloride, which originate from the reaction. For this variation, onium hydrochloride is preferred.

For a particularly preferred variation, onium carboxylates of any amines are used. This method has the advantage of a milder reaction and a higher yield in comparison to methods of the state of the art, for which trialkylamine is used as base. This option will be explained in greater detail hereinafter.

R$^1$ preferably represents methyl, ethyl, n-propyl or i-propyl or methyl, ethyl, n-propyl or i-propyl, substituted by at least one fluorine atom. It is particularly preferred if R$^1$ represents methyl, ethyl or methyl or ethyl, substituted by at least one fluorine atom. It is especially preferred if R$^1$ represents CF$_3$, CF$_2$H, CF$_2$Cl, C$_3$F$_7$ or CF$_3$C(O)CH$_2$.

R$^2$ may represent aryl, for example phenyl or C1 to C4 alkyl groups and/or phenyl substituted by halogen atoms. Preferably, R$^2$ represents linear or branched C1 to C4 alkyl. It is particularly preferred if R$^2$ represents methyl, ethyl, n-propyl or i-propyl.

The molar ratio of "onium" salt to acid halide or acid anhydride advantageously is between 0.1:1 and 2:1.

Acid chloride is preferred as the acid halide. For simplicity, the invention will be described further hereinafter with reference to this preferred embodiment. It should be understood, however, that other acid halides can be used in the method of the invention.

The molar ratio of acid chloride or anhydride to vinyl ether advantageously is between 0.9:1 and 1:0.8.

The reaction is carried out at a temperature of, for example, −15° to +80° C. and advantageously at a temperature ranging from 0° to 40° C. It may be exothermic, so that the reaction mixture may optionally have to be cooled or the reaction carried out very slowly.

Pursuant to preferred embodiment, a solvent is used for the reaction. This is advantageous particularly if, initially, the vinyl ether and then the anhydride are added to the "onium" salt or an amine. Aliphatic linear or branched hydrocarbons or aliphatic linear or branched halogenated hydrocarbons, cyclic aliphatic hydrocarbons or esters of trifluoroacetic acid or of pentafluoropropionic acid, for example, are suitable. Optionally halogenated hydrocarbon compounds with 1 to 8 carbon atoms are highly suitable. Particularly suitable are, for example, dichloromethane, 1,1,1-trifluoro-2,2,2-trichloroethane, hexane, cyclohexane, ethyl trifluoroacetate or propyl trifluoroacetate.

In accordance with a different preferred embodiment, no solvent is used for the reaction between the anhydride and the vinyl ether. This is readily possible particularly if, initially, the anhydride and then the vinyl ether are added to the "onium" salt or the amine. It is, of course, advantageous that a solvent does not have to be removed, since there are no recovery costs and the energy required is less.

Finally, it is also possible to carry out the reaction between the vinyl ether and the acid halide in the absence of a solvent and then, to improve the phase separation, to add a solvent such as $CH_2Cl_2$.

The anion of the carboxylic acid of the "onium" salt preferably has the formula $R'C(O)O^-$, R' having the meaning given above. The carboxylic acid of the "onium" salt used is preferably the acid which corresponds to the acid halide used.

As used herein, the term "onium" refers to cations with a positively charged nitrogen, such as protonated aromatic nitrogen bases, like pyridinium, or protonated alkylammonium, dialkylammonium or trialkylammonium cations or it refers to cycloalkyl-substituted ammonium compounds or cycloaliphatic nitrogen bases, such as piperidinium or quaternary ammonium cations.

"Onium" cations of nitrogen, having the formula $R'R''R'''R''''N^+$ are very suitable as carboxylic acid salt. R', R'', R''' and R'''' independently of one another represent hydrogen, alkyl with 1 to 20 carbon atoms, aryl or aralkyl. R' and R'' or R''' and R'''', or R', R'' and R''' or R', R'', R''' and R'''' may also, optionally with inclusion of the nitrogen atom, form saturated or unsaturated ring systems. In this context, the term "aryl" denotes phenyl or phenyl substituted by one or more C1–C2 alkyl groups. Outstandingly suitable are salts, in which the "onium" represents ammonium, pyridinium or $R^{1'}R^{2'}R^{3'}R^{4'}N^+$, in which $R^{1'}$, $R^{2'}$, $R^{3'}$ and $R^{4'}$ independently of one another represent hydrogen, alkyl with 1 to 15 carbon atoms, phenyl or benzyl. Examples of such cations include pyridinium, piperidinium, N-methylpiperidinium, anilium, benzyltriethylammonium and triethylammonium.

Amines, especially cycloaliphatic amines, substituted by hydroxy groups and, in particular, hydroxy-substituted piperidine and N—C1–C4 alkylpiperidine are also usable. For example, piperidines substituted at the C4 atom, such as 4-hydroxypiperidine, N-methyl-4-hydroxypiperidine, N-ethyl-4-hydroxypiperidine and N-propyl-4-hydroxypiperidine, are suitable.

Cations of amines, which are disclosed in published US patent application no. 2004/097,758 (=DE 101 04 663) are also usable. They are "onium" cations based on a monocyclic or bicyclic compound with at least two nitrogen atoms, at least one nitrogen atom being incorporated in the ring system.

Accordingly, "onium" cations, based on monocyclic compounds, can be used. They are saturated or unsaturated 5-membered, 6- membered or 7- membered ring compounds. At least one nitrogen atom is incorporated in the ring. A further nitrogen atom may also be incorporated in the ring system. Alternatively or additionally, the ring may be substituted by one or more amino groups. Dialkylamino groups, in which the alkyl groups may be the same or different and comprise 1 to 4 carbon atoms, are preferred. The amino group may also represent a saturated ring system, such as a piperidino group. Readily usable representatives of monocyclic ring systems include dialkylaminopyridine, dialkylaminopiperidine and dialkyl-aminopiperazine.

"Onium" cations of bicyclic compounds may also be used. Here also, one, two or more nitrogen atoms may be integrated in the ring system. The compounds may be substituted by one or more amino groups. Once again, dialkylamino groups are preferred; the alkyl groups may be the same or different and comprise one to four carbon atoms or, together with the nitrogen atom, form a saturated ring system, such as the piperidinyl group.

From the foregoing, it is clear that, for this embodiment, at least two nitrogen atoms in the usable compounds must have basic properties and, depending on the nature of the bonds, be linked to two or three carbon atoms.

"Onium" salts of carboxylic acids and bicyclic amines, especially 1,5-diazabicyclo[4.3.0]-5-nonene (DBN) and 1,8-diazabicyclo[5.4.0.]-7-undecene (DBU), are particularly preferred. The "onium" salts of aromatic amines, particularly those with one, two or three electron-displacing groups, such as C1 to C3 alkyl groups, such as salts of 2-picoline, can also readily be used. Salts of picoline, chlorinated in the ring, for example, in the 4 position, and/or in the alkyl groups, such as the trifluoroacetic acid adducts of 2-chloromethylpicoline, 2-dichloromethylpicoline and 2-trichloromethylpicoline, are liquids and can therefore even act as a solvent.

The "onium" salts of carboxylic acids can be synthesized by a simple reaction of the corresponding amines and the free acids.

The inventive method of synthesizing alkenones of formula (I) can be carried out at an elevated pressure and also at ambient pressure. It can be carried out batchwise or semi-continuously.

The reaction mixture is worked up by conventional methods. For example, after removal of the solvent (if any is contained), the desired alkenone of formula (I) can be isolated from the mixture by distillation. A different possibility is to treat the reaction mixture with water and, after removing the water by conventional means, such as sodium sulfate, isolate the alkenone from the organic phase.

A preferred embodiment employs a work-up method involving the formation of two phases. For this purpose, two particularly advantageous variations are available. According to one variation, water is added for the working up. An organic phase is formed, which contains the desired product as well as the organic solvent used. The aqueous phase contains the consumed "onium" salt. If the acid anhydride has been used as one of the educts, the "onium" salt is present largely as the "onium" salt of the carboxylic acid corresponding to the anhydride. If the "onium" salt of the carboxylic acid has been used as acid interceptor, an excess of acid will be present in the aqueous phase. If the "onium" salt is to be used again as acid interceptor, the ratio of "onium" cation to carboxylic acid content must once again be brought into the preferred range of 0.9:1 to 1:0.9. This is most easily achieved by adding sufficient alcohol, such as a C1 to C4 aliphatic alcohol, so that the acid, present in excess of the desired content, is reacted by esterification and can be removed by distillation together with the water present.

If the acid chloride, for example, is used as educt, the "onium" salt is present in the aqueous phase largely as the hydrochloride or as an onium complex enriched with chloride. In order to work up the reaction mixture, it is treated with the corresponding carboxylic acid, such as trifluoroacetic acid, in a 5-fold to 10-fold molar excess. The hydrochloric acid released is evaporated at elevated temperature. Since an excess of carboxylic acid is usually used for this regeneration, an "onium" salt of the carboxylic acid with an excess of the acid, which is not very suitable for being re-used, is then present once again. As already described above, an alcohol is then added, which reacts with the acid with formation of the ester. The ester can then be distilled off, with water being distilled off at the same time.

In accordance with a different embodiment, an organic solvent is added, which brings about the formation of two phases. In order to achieve this, it is necessary to initially remove any solvents which cause the reaction mixture to exist as a homogeneous phase. A solvent or solvent mixture is then added, which brings about the separation into two phases. The following solvents, for example, have proven to be useful: ether, especially dialkyl ether, particularly diethyl ether, esters of trifluoroacetic acid, such as propyl trifluoroacetate, aliphatic hydrocarbons, such as hexane, cyclic hydrocarbons, such as cyclohexane, halogenated hydrocarbons, such as 1,1,2-trichloro-1,2,2-trifluoroethane (CFC-113) or dichloromethane. By a simple trial and error procedure, someone, skilled in the art, can easily find further solvents, which also induce the formation of two phases.

One phase contains the solvent and the alkenone formed and the other phase contains essentially the salt. The phase which contains the alkenone is separated, the solvent is removed, and the alkenone is purified by conventional means, for example, by distillation, if such a procedure is necessary at all, because the product generally is obtained in very high purity. It has been found that, for this embodiment also, the yield and purity of the product are very high.

Instead of the reaction with a carboxylic acid such as trifluoroacetic acid, the regeneration can also to be carried out by addition of the anhydride of the carboxylic acid, for example, by the addition of acetic anhydride or trifluoroacetic anhydride, preferably by the addition of the anhydride of the carboxylic acid, which corresponds to the acid chloride used. The acid chloride and the "onium" salt of the carboxylic acid are then formed, which can then be reacted further with vinyl ethers in accordance with the method of the invention.

The "onium" salt of the carboxylic acid can be synthesized initially by reacting the free base with the carboxylic acid. It can also be synthesized during the reaction by passing the anhydride of the carboxylic acid, which corresponds to the acid chloride, continuously or discontinuously into the reaction mixture.

According to a modification of the method of the invention, an aldehyde or acid chloride corresponding to formula (II) and a vinyl ether corresponding to formula (III) are reacted, in a first step, in the presence of an amine base, as described, for example, in U.S. Pat. No. 5,708,175. The resulting amine hydrochloride is then regenerated, preferably as described above, and used once again in the method of the invention in a second step of this embodiment.

The invention also relates to adducts of a carboxylate anion corresponding to the formula $R^1C(O)O^-$ with a protonated cation of pyridine, which is substituted by one, two or three C1 to C3 alkyl groups, preferably by one, two or three methyl groups. Preferably, these are adducts with the anion of trifluoroacetic acid. In this regard, these adducts may additionally contain up to 1 mole of the free acid per mole of "onium" salt.

The protonated cation of pyridine, substituted by one to three C1 to C3 alkyl groups, may also be chlorinated, especially in the alkyl groups. Accordingly, it may be 2-chloromethylpyridinium, 2-dichloromethylpyridinium or 2-trichloromethylpyridinium. Picolinium trifluoroacetate (n=0) as well as an adduct of trifluoroacetic acid, especially one having the formula $A-B_n$, in which A represents picolinium trifluoroacetate, B represents trifluoroacetic acid and $0<n\leq 2$, is particularly preferred.

The invention additionally relates to the use of pyridine, which is substituted by one, two or three C1 to C3 alkyl groups, as acid interceptor. 2-Alkylpyridine, in which alkyl represents methyl, ethyl or propyl, is preferred.

EXAMPLES

The following examples are intended to illustrate the invention in further detail without limiting its scope. Examples 1 to 8 explain the synthesis using trifluoroacetyl chloride and examples 9 to 12 explain the synthesis using trifluoroacetic anhydride. Example 13 explains the regeneration of the "onium" salt consumed with trifluoroacetic acid. Examples 1 to 3 involve an aqueous work-up.

Example 1

Synthesis of
4-ethooxy-1,1,1-trifluoro-3-butene-2-one (ETFBO)
with pyridinium trifluoroacetate Reaction:

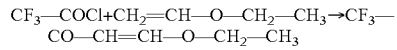

Formulation:

| | | |
|---|---|---|
| pyridine | 0.4 moles | 31.6 g |
| trifluoroacetic acid (TFA) | 0.4 moles | 45.6 g |
| ethyl vinyl ether | 0.3 moles | 21.6 g |
| trifluoroacetyl chloride (TFAC) | 0.3 moles | 39.6 g |
| dichloromethane | | 180.0 g |

Procedure:

To begin with, pyridinium trifluoroacetate was prepared in a 500 ml 3-neck flask with a dry ice condenser. For this purpose, the pyridine was added to the flask and the TFA was added dropwise with stirring. Since the reaction is strongly exothermic, the flask was cooled in a water bath to prevent excessive heating. Subsequently, dichloromethane and ethyl vinyl ether were added, and TFAC was introduced with stirring. The reaction temperature was kept at room temperature by the water bath. When the TFAC was introduced, the formulation became slightly yellowish. Subsequently, the formulation was stirred for 2¾ hours at room temperature, after which time a sample was taken for gas chromatography analysis (GC) (sample was hydrolyzed). The conversion was 97.2% and the selectivity for the formation of 4-ethoxy-1,1,1-trifluoro-3-buten-2-one (EFTBO) was quantitative.

In order to work up the reaction mixture, water was added and the resulting two phases were separated. The dichloromethane was distilled off from the organic phase, and the remaining product was precision distilled. Trifluoroacetic acid was added to the aqueous phase, and the mixture was refluxed to drive off the hydrogen chloride. Ethanol was then added in an amount corresponding to the excess of trifluoroacetic acid used, and the resulting trifluoroacetate ester, together with ethanol and water, was distilled off as an azeotrope. The "onium" salt of trifluoroacetic acid remaining was then used again for the synthesis of ETFBO.

Example 2

Trifluoroacetylation of Ethyl Vinyl Ether with the Trifluoroacetic Acid (TFA) Salt of 1,5-diazabicyclo[4.3.0]-5-none (DBN) [TFAC Deficiency]

Reaction:

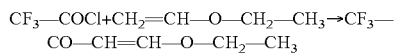

Formulation:

| DBN | 0.2 moles | 24.8 g |
| TFA. | 0.2 moles | 22.8 g |
| Ethyl vinyl ether | 0.2 moles | 14.2 g |
| TFAC | 0.18 moles | 23.8 g |
| Dichloromethane | | 120.0 g |

Procedure:

To begin with, DBN×TFA was prepared in a 250 ml 3-neck flask with a dry ice condenser. For this purpose, DBN was added to the flask and the TFA was added dropwise with stirring. Since the reaction is strongly exothermic, the flask was cooled in a water bath to prevent excessive heating. The DBN×TFA became solid. Subsequently, dichloromethane and ethyl vinyl ether were added, and TFAC was introduced with stirring. The reaction temperature was kept at room temperature by the water bath. When the TFAC was introduced, the formulation became yellow. Subsequently, the formulation was stirred for one hour at room temperature, after which time a sample was taken for gas chromatographic analysis (GC) (sample was hydrolyzed). The conversion of EVE was quantitative, and the selectivity for the formation of EFTBO was 93.4%. The reaction mixture was worked up as in Example 1.

Example 3

Trifluoroacetylation of Ethyl Vinyl Ether with DBN×TFA [TFAC Equimolar]

Reaction:

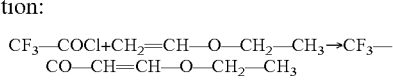

Formulation:

| DBN | 0.05 moles | 6.2 g |
| TFA | 0.05 moles | 5.7 g |
| Ethyl vinyl ether | 0.05 moles | 3.6 g |
| TFAC | 0.05 moles | 6.6 g |
| Dichloromethane | | 30.0 g |

Procedure:

To begin with, DBN×TFA was prepared in a 100 ml 3-neck flask. For this purpose, dichloromethane with DBN was added to the flask, and TFA was added dropwise with stirring. Since the reaction is strongly exothermic, the flask was cooled in a water bath to prevent excessive heating. Subsequently, ethyl vinyl ether was added, and TFAC was introduced with stirring. The reaction temperature was kept at room temperature by the water bath. When the TFAC was introduced, the formulation became yellow. Subsequently, the formulation was stirred for 1½ hours at room temperature, after which time a sample was taken for gas chromatographic analysis (GC) (sample was hydrolyzed). The conversion of EVE was quantitative, and the selectivity to ETFBO was 95%. The product was worked up as in Example 1.

Example 4

Trifluoroacetylation of Ethyl Vinyl Ether with DBN×TFA with Formation of Two Phases Reaction:

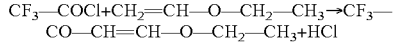

Formulation:

| DBN | 0.20 moles | 24.8 g |
| TPA | 0.20 moles | 22.8 g |
| ethyl vinyl ether | 0.15 moles | 10.8 g |
| TFAC | 0.15 moles | 90.0 g |

Procedure:

To begin with, DBN×TFA was prepared in a 250 ml 3-neck flask. For this purpose, dichloromethane and DBN were added to the flask, and TFA was added dropwise with stirring. Since the reaction is strongly exothermic, the flask was cooled in a water bath to prevent excessive heating. Subsequently, ethyl vinyl ether was added, and TFAC was introduced with stirring. The reaction temperature was kept at room temperature by the water bath. When the TFAC was introduced, the formulation became orange. Subsequently, the formulation was stirred for two hours at room temperature, after which time a sample was taken for gas chromatographic (GC) analysis (sample was hydrolyzed). The ethyl vinyl ether had reacted completely. The solvent, dichloromethane, was then evaporated under vacuum in a rotary evaporator, and the remaining solution was divided into several partial volumes, which were worked up by treatment with a solvent which formed a second phase.

The partial volumes were treated with equal parts by volume of the following solvents:

Example 4.1

Diethyl Ether

Example 4.2

Propyl Trifluoroacetate

Example 4.3

Hexane

Example 4.4

Cyclohexane

Example 4.5

1,2-trichloro-1,2,2-trifluoroethane (113)

Work-Up:

The organic phase contained mainly the desired product ETFBO; the amine salt consumed was contained quantitatively in the other phase. The ETFPO phase was separated and isolated gently, with a purity in excess of 98%, in a rotary evaporator by evaporating the solvent under vacuum.

Example 5

Trifluoroacetylation of Ethyl Vinyl Ether with DBU×TFA (DBU=1,5-diazabicyclo [5.4.0]-5-undecene)

Reaction:

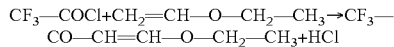

ETFBO

Formulation:

| DBU | 0.2 moles | 30.4 g |
| TFA | 0.2 moles | 22.8 g |
| Ethyl vinyl ether | 0.15 moles | 10.8 g |
| TFAC | 0.15 moles | 19.8 g |
| Dichloromethane (MeCl$_2$) | | 90.0 g |

Procedure:

To begin with, DBU×TFA was prepared in a 250 ml 3-neck flask. For this purpose, dichloromethane with DBU was added to the flask, and TFA was added dropwise with stirring. Since the reaction is strongly exothermic, the flask was cooled in a water bath to prevent excessive heating. Subsequently, ethyl vinyl ether was added, and TFAC was introduced with stirring. The reaction temperature was kept at room temperature by the water bath. When the TFAC was introduced, the formulation became orange. Subsequently, the formulation was stirred for two hours at room temperature, after which time a sample was taken for gas chromatographic (GC) analysis (sample was hydrolyzed). A second sample was drawn the next morning (the formulation had become dark). The ethyl vinyl ether had reacted completely to EFTBO. The isolation was carried out by the two-phase method described in Example 4.

Example 6

Trifluoroacetylation of Ethyl Vinyl Ether with Pyridine×TFA

Reaction:

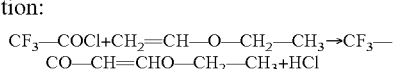

ETFBO

Formulation:

| Pyridine | 0.4 moles | 31.6 g |
| TFA | 0.4 moles | 45.6 g |
| Ethyl vinyl ether | 0.3 moles | 21.6 g |
| TFAC | 0.3 moles | 39.6 g |
| Dichloromethane | | 180.0 g |

Procedure:

To begin with, pyridinium trifluoroacetate was prepared in a 500 ml 3-neck flask. For this purpose, pyridine was added to the flask, and TFA was added dropwise with stirring. Since the reaction is strongly exothermic, the flask was cooled in a water bath to prevent excessive heating. Subsequently, dichloromethane and ethyl vinyl ether were added, and TFAC was introduced with stirring. The reaction temperature was kept at room temperature by the water bath. When the TFAC was introduced, the formulation became slightly yellowish. Subsequently, the formulation was stirred for 2¾ hours at room temperature, after which time a sample was taken for gas chromatographic (GC) analysis (sample was hydrolyzed). The ethyl vinyl ether had reacted almost completely. The conversion to 4-ethoxy-1,1,1-trifluoro-3-buten-2-one (ETFBO) was 97.2%. The methylene chloride was evaporated under vacuum in a rotary evaporator, and the remaining solution was divided once again into partial volumes and extracted with a solvent, which forms a second phase.

The partial volumes formed a second phase with equal parts by volume of the following solvents:

Example 6.1

Hexane

Example 6.2

Cyclohexane

Example 6.3

1,1,2-trichloro-1,2,2-trifluoroethane (113)

This second phase once again contained mainly the desired product ETFBO. The other phase quantitatively contained the amine that had been consumed. The EFTBO phase was then separated, and the product was isolated gently with a purity of more than 98% by evaporating the solvent under vacuum in a rotary evaporator. Working up by forming two phases as described in Examples 4 to 6 led to particularly high yields without any thermal effect on the reaction mixture.

Example 7

Trifluoroacetylation of Ethyl Vinyl Ether/Use of Picoline

Reaction:

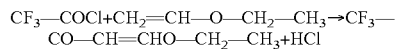

$CF_3$—COCl+$CH_2$=CH—O—$CH_2$—$CH_3$→$CF_3$—CO—CH=CHO—$CH_2$—$CH_3$+HCl

Formulation:

| 2-Picoline | 0.20 moles | 18.6 g |
| --- | --- | --- |
| TFA | 0.20 moles | 22.8 g |
| Ethyl vinyl ether | 0.15 moles | 10.8 g |
| TFAC | 0.15 moles | 19.8 g |
| Dichloromethane | | 90.0 g |

Procedure:

To begin with, picoline trifluoroacetate was prepared in a 250 ml 3-neck flask with a dry-ice condenser. For this purpose, dichloromethane and 2-picoline were added to the flask, and TFA was added dropwise with stirring. Since the reaction is strongly exothermic, the flask was cooled in a water bath to prevent excessive heating. Subsequently, ethyl vinyl ether was added, and TFAC was introduced with stirring. The reaction temperature was kept at room temperature by the water bath. When the TFAC was introduced, the formulation turned yellow. Subsequently, the formulation was stirred for a further 2½ hours at room temperature, after which time a sample was taken for gas chromatographic (GC) analysis (sample was hydrolyzed). The ethyl vinyl ether had reacted completely. The formulation was now added to 150 g of ice water, and the organic phase was washed twice with water and distilled using a rotary evaporator.

The dichloromethane was removed at a water bath temperature of 28° C. and a pressure of 300 mbar. The 4-ethoxy-1,1,1-trifluoro-3-buten-2-one was distilled at a water bath temperature of 64° C. and a pressure of 13 mbar. According to the gas chromatogram, the purity was 98.0%. The yield of ETFBO was 94.6%.

Example 8

Trifluoroacetylation of Ethyl Vinyl Ether, First Step: Free Base, Second Step: "Onium" Trifluoroacetate as Acid Interceptor Step 1:

Formulation for First Step

| 2-Picoline | 0.05 moles | 4.66 g |
| --- | --- | --- |
| Ethyl vinyl ether | 0.15 moles | 10.8 g |

-continued

| TFAC | 0.15 moles | 19.8 g |
| --- | --- | --- |
| Dichloromethane | | 90.0 g |

Procedure for First Step:

2-Picoline, dichloromethane and ethyl vinyl ether were added to a 250 ml 3-neck flask with a dry-ice condenser, and TFA was added with stirring. The reaction temperature was kept at room temperature by a water bath. When the TFAC was introduced, the formulation turned yellow. After 2½ hours, the ethyl vinyl ether had reacted completely, and the formulation was added to 150 g of ice water and washed twice with water. The organic phase was then distilled using a rotary evaporator. The dichloromethane was removed at a water bath temperature of 24° C. and a pressure of 300 mbar. The 4-ethoxy-1,1,1-trifluoro-3-buten-2-one distilled over at a water bath temperature of 65° C. and a pressure of 15 mbar. According to gas chromatography, the purity was 97.4%. The yield of EFTBO was 76.2%.

The remaining residue is comprised largely of picoline hydrochloride. The residue was treated with trifluoroacetic acid; the hydrogen chloride was driven off, and ethanol was added in order to convert excess trifluoroacetic acid to the ester (see also Example 12c). The resulting picolinium trifluoroacetate was then used in the second step.

Step 2: Use of the Picolinium Trifluoroacetate Produced in Step 1

As in Example 7, the picoline and the trifluoroacetic acid were used in the form of the "onium" salt obtained above, instead of being used separately.

Example 9

Trifluoroacetylation of Ethyl Vinyl Ether/Use of Trifluoroacetic Anhydride (TFAH)

Reaction:

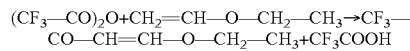

$(CF_3$—CO$)_2$O+$CH_2$=CH—O—$CH_2$—$CH_3$→$CF_3$—CO—CH=CH—O—$CH_2$—$CH_3$+$CF_3$COOH

Formulation:

| 2-Picoline | 0.20 moles | 18.6 g |
| --- | --- | --- |
| TFA | 0.20 moles | 22.8 g |
| Ethyl vinyl ether | 0.15 moles | 10.8 g |
| TFAH | 0.15 moles | 31.5 g |
| Dichloromethane | | 90.0 g |

Procedure:

To begin with, picoline trifluoroacetate was prepared in a 250 ml 3-neck flask with a water-cooled condenser. For this purpose, dichloromethane and 2-picoline were added to the flask, and TFA was added dropwise with stirring. Since the reaction is strongly exothermic, the flask was cooled in a water bath to prevent excessive heating. Subsequently, ethyl vinyl ether was added, and TFAH was introduced with stirring. The reaction temperature was kept at room temperature by the water bath. When the TFAH was introduced, the formulation turned yellow. Subsequently, the formulation was stirred for one hour, after which time a sample was taken for gas chromatographic (GC) analysis (sample was hydrolyzed). A further sample was taken the next morning.

The ethyl vinyl ether had reacted completely. The formulation was then added to 150 g of ice water, and the organic phase was washed twice with water and distilled using a rotary evaporator.

The dichloromethane was removed at a water bath temperature of 24° C. and a pressure of 300 mbar. The 4-ethoxy-1,1,1-trifluoro-3-buten-2-one distilled over at a water bath temperature of 68° C. and a pressure of 18 bar. According to gas chromatography, the purity was 97.9%. The yield of ETFBO was 87.96%.

Example 10

Trifluoroacetylation of Ethyl Vinyl Ether/Use of Trifluoroacetic Anhydride and Picoline Reaction:

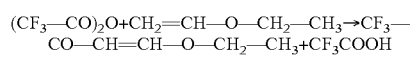

Formulation:

| Pyridine | 0.20 moles | 15.8 g |
| TFA | 0.20 moles | 22.8 g |
| Ethyl vinyl ether | 0.15 moles | 10.8 g |
| TFAH | 0.15 moles | 31.5 g |
| Dichloromethane | | 90.0 g |

Procedure:

To begin with, pyridine trifluoroacetate was prepared in a 250 ml 3-neck flask with a water-cooled condenser. For this purpose, dichloromethane and pyridine were added to the flask, and TFA was added dropwise with stirring. Since the reaction is strongly exothermic, the flask was cooled in a water bath to prevent excessive heating. Subsequently, ethyl vinyl ether was added, and TFAH was added dropwise with stirring. The reaction temperature was kept at room temperature by the water bath. Stirring was continued for one hour at room temperature, after which time a sample was taken for gas chromatographic (GC) analysis (sample was hydrolyzed). A further sample was taken the next morning. The ethyl vinyl ether had reacted completely. The yield of ETFBO was 85.0%.

The reaction mixture was worked up by adding water and treating the resulting organic phase as described above in that the dichloromethane was distilled off and the product was precision distilled. Ethanol was added to the aqueous phase, and an azeotrope of ester, water and ethanol was distilled off.

Example 11

Trifluoroacetylation of Ethyl Vinyl Ether/Use of DBN

Reaction:

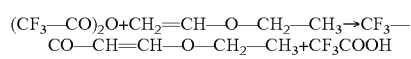

Formulation:

| DBN | 0.20 moles | 24.8 g |
| TFA | 0.20 moles | 22.8 g |
| Ethyl vinyl ether | 0.15 moles | 10.8 g |
| TFAH | 0.15 moles | 31.5 g |
| Dichloromethane | | 90.0 g |

Procedure:

To begin with, DBN×TFA was prepared in a 250 ml 3-neck flask with a water-cooled condenser. For this purpose, dichloromethane and DBN were added to the flask, and TFA was added dropwise with stirring. Since the reaction is strongly exothermic, the flask was cooled in a water bath to prevent excessive heating. Subsequently, ethyl vinyl ether was added, and TFAH was added dropwise with stirring. The formulation turned yellow. Subsequently, stirring was continued for 1½ hours at room temperature, after which time a sample was taken for gas chromatographic (GC) analysis (sample was hydrolyzed). The ethyl vinyl ether had reacted completely. The dichloromethane was evaporated under vacuum at room temperature in a rotary evaporator, and the remaining solution was divided into partial volumes and extracted with different solvents, which formed two phases. Hexane, pentane, cyclohexane and 113 were used as two-phase extraction agents. The total yield of ETFBO isolated was 91%.

Example 12

Working up. "Onium" Hydrochloride

Example 12a

Working up Pyridinium Hydrochloride

Reaction:

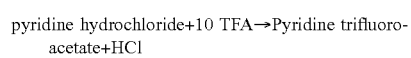

Formulation:

| Pyridine hydrochloride | 0.05 moles | 5.8 g |
| TFA | 0.50 moles | 75.0 g |

Procedure:

Pyridine hydrochloride and TFA were added to a 100 ml 3-neck flask with a water-cooled condenser and refluxed. Cl⁻ samples were taken after 5, 8 and 15 hours.

Cl⁻ Analyses

| Sample | Time in hours | % Cl⁻ |
|---|---|---|
| 1 | 0 | 2.71 |
| 2 | 5 | 0.67 |
| 3 | 8 | 0.54 |
| 4 | 15 | 0.50 |

Example 12b

Working-up Picolinium Hydrochloride

Reaction:

Picoline hydrochloride+10 TFA→picoline trifluoroacetate+HCl

Formulation:

| Pyridine hydrochloride | 0.16 moles | 20.6 g |
| TFA | 1.60 moles | 182.4 g |

Procedure:
Pyridine hydrochloride and TFA were added to a 250 ml 3-neck flask with water-cooled condenser and refluxed. Cl⁻ samples were taken after 1 and 7 hours.

Cl⁻ Analyses

| Sample | Time in hours | % Cl⁻ |
|---|---|---|
| 1 | 0 | 2.40 |
| 2 | 1 | 0.26 |
| 3 | 7 | 0.027 |

In comparison to pyridine, it was easier to exchange the chloride.

Example 12c

Conversion with Ethanol

The reaction product of Example 12a) was heated, and excess trifluoroacetic acid was distilled off until picoline trifluoroacetate with additional trifluoroacetic acid was present as adduct. Two moles of trifluoroacetic acid (amine×3 TFA) per mole of picolinium trifluoroacetate were present in the residue. It was not possible to remove more trifluoracetic acid from this adduct by distillation. One mole of ethanol was added per mole of acetic acid. After the ethyl trifluoroacetate was distilled off, some unreacted ethanol and water present also distilled over. The picolinium trifluoroacetate remained behind and was returned to the reaction.

Example 13

Trifluoroacetylation of Ethyl Vinyl Ether Without Adding a Solvent

Reaction:

$(CF_3-CO)_2O + CH_2=CHO-CH_2-CH_3 \rightarrow CF_3-CO-CH=CH-O-CH_2-CH_3 + CF_3COOH$ Formulation:

| 2-Picoline | 0.10 moles | 9.3 g |
| TFA | 0.10 moles | 11.4 g |
| Ethyl vinyl ether | 0.15 moles | 10.8 g |
| TFAH | 0.15 moles | 31.5 g |

Procedure:
To begin with, picoline trifluoroacetate was prepared in a 100 ml 3-neck flask with a water-cooled condenser. For this purpose, 2-picoline was added to the flask, and TFA was added dropwise with stirring. Since the reaction is strongly exothermic, the flask was cooled in a water bath to prevent excessive heating. Subsequently, TFAH was added, and ethyl vinyl ether was added dropwise with stirring (reaction strongly exothermic). The reaction mixture was kept at room temperature by ice water. The formulation turned yellow during the addition of the TFAH. Stirring was continued for one hour at room temperature, after which time a sample was taken for gas chromatographic (GC) analysis (sample was hydrolyzed). The conversion to EFTBO was 91.3%.

Example 14

Trifluoroacetylation in the Absence of a Solvent, Phase Separation with Addition of Solvent Procedure:
Example 13 was repeated. The reaction was carried out without a solvent. Dichloromethane was then added to improve the phase separation. Once again, a high conversion to EFTBO was noted.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:
1. A method of synthesizing an alkenone compound corresponding to the formula:

$$R^1-C(O)-C(H)=C(H)-OR^2 \quad (I)$$

wherein
  $R^1$ represents a C1 to C4 alkyl group or a C1 to C4 alkyl group substituted by at least one halogen atom, or $R^1$ represents $CF_3C(O)CH_2$; and
  $R^2$ represents aryl, substituted aryl, a C1 to C4 alkyl group or a C1 to C4 alkyl group, which is substituted by at least one halogen atom;
said method comprising:
reacting an acid anhydride or an acid halide corresponding to formula (II)

$$R^1-C(O)X \quad (II)$$

wherein
X represents $R^1-C(O)-O$ or fluorine, chlorine or bromine and $R^1$ has the meaning given above,
with a vinyl ether corresponding to formula (III)

$$CH_2=C(H)-OR^2 \quad (III)$$

wherein $R^2$ has the meaning given above,
in the presence of an "onium" salt of a carboxylic acid.

2. A method according to claim 1, wherein $R^1$ represents methyl, ethyl or propyl, or methyl, ethyl or propyl, substituted by at least one fluorine atom.

3. A method according to claim 1, wherein $R^1$ represents $CF_3$, $CF_2H$, $CF_2Cl$, $C_2F_5$ or $CF_3C(O)CH_2$.

4. A method according to claim 1, wherein $R^2$ represents methyl, ethyl, n-propyl or isopropyl.

5. A method according to claim 1, wherein the "onium" salt and acid halide are present in a molar ratio of between 0.1 1 and 2:1.

6. A method according to claim 5, wherein the acid halide is an acid chloride.

7. A method according to claim 1, wherein the reaction is carried out at a temperature in the range from −15° C. to +80° C.

8. A method according to claim 7, wherein the reaction is carried out at a temperature in the range from 0° C. to 40° C.

9. A method according to claim 1, wherein the reaction mixture is separated into two phases, one of which contains the alkenone product.

10. A method according to claim 9, wherein the separation into two phases is induced by adding an organic solvent, and the alkenone is in the organic phase, and the "onium" salt is in the other phase.

11. A method according to claim 9, comprising adding water to the reaction mixture to obtain an aqueous phase enriched with "onium" halide; treating the onium complex in the aqueous phase with trifluoroacetic acid; driving off hydrogen chloride which forms; adding an alcohol to the residue to form an ester with excess trifluoroacetic acid; separating the ester, and recovering resulting "onium" trifluoroacetate.

12. A method according to claim 1, wherein "onium" halide formed in the reaction is regenerated with an anhydride of a carboxylic acid.

13. A method according to claim 1, wherein a first step of the method is carried out in the presence of the free base corresponding to the "onium" salt of the carboxylic acid; the "onium" halide formed is regenerated with formation of the "onium" salt of the carboxylic acid, and the salt is used in a subsequent step of the method.

* * * * *